United States Patent [19]

Grieshaber

[11] 4,144,883

[45] Mar. 20, 1979

[54] SPIROMETER

[76] Inventor: Eugen Grieshaber, Höchst 5, 7821 Eisenbach, Fed. Rep. of Germany

[21] Appl. No.: 784,374

[22] Filed: Apr. 4, 1977

[30] Foreign Application Priority Data

Apr. 6, 1976 [DE] Fed. Rep. of Germany ....... 2614752

[51] Int. Cl.² .......................... A61B 5/08; G01F 1/06
[52] U.S. Cl. ..................... 128/2.08; 272/99; 73/229
[58] Field of Search ......... 128/2.08; 272/99; 73/229, 230; 116/129 B

[56] References Cited

U.S. PATENT DOCUMENTS

| | | | |
|---|---|---|---|
| 400,331 | 3/1889 | Graeser | 73/230 |
| 638,073 | 11/1899 | Smith | 73/229 |
| 644,487 | 2/1900 | Zumkeller | 73/229 |
| 764,546 | 7/1904 | Bardsley | 128/2.08 |
| 966,050 | 8/1910 | Ramage | 128/2.08 |
| 1,018,582 | 2/1912 | Nelson | 116/129 B X |
| 1,683,103 | 9/1928 | Schlaich | 116/129 B |
| 1,895,023 | 1/1933 | Chrisman et al. | 73/230 |
| 2,346,037 | 4/1944 | McCormick | 73/229 |
| 3,911,743 | 10/1975 | Nicolas et al. | 73/229 |
| 3,949,737 | 4/1976 | Nielsen | 272/99 |

FOREIGN PATENT DOCUMENTS

| | | | |
|---|---|---|---|
| 722220 | 7/1942 | Fed. Rep. of Germany | 128/2.08 |
| 1248226 | 8/1967 | Fed. Rep. of Germany | 128/2.08 |
| 1548637 | 8/1969 | Fed. Rep. of Germany | 116/129 B |
| 1775 of | 1914 | United Kingdom | 73/230 |

Primary Examiner—Jerome Schnall
Attorney, Agent, or Firm—McGlew and Tuttle

[57] ABSTRACT

The spirometer comprises a housing having walls defining a turbine chamber, an antechamber having a blow-in opening and having an annular portion around it and a plurality of passages extending from the annular portion tangentially into the turbine chamber. A shaft extends through the turbine chamber and an air wing rotor is secured to the shaft and is located in the turbine chamber for rotation by the blowing air directed in through the blowing opening and the antechamber and through the passages into the turbine chamber. The housing has a portion with a dial having indications thereon and a pointer and a drag pointer rotatably mounted in the housing over the dial and is movable over the dial to indicate the blowing rate. A reduction gearing is connected between the shaft and the pointer and the drag pointer to rotate the pointer and the drag pointer upon rotation of the shaft. A manually operable, disconnectable coupling is connected between the shaft and the pointer for disengaging the pointer. A zero return spring acts on the pointer to bias it towards a zero position and a return knob is connected to the drag pointer for moving it manually back to zero separately from the pointer.

14 Claims, 6 Drawing Figures

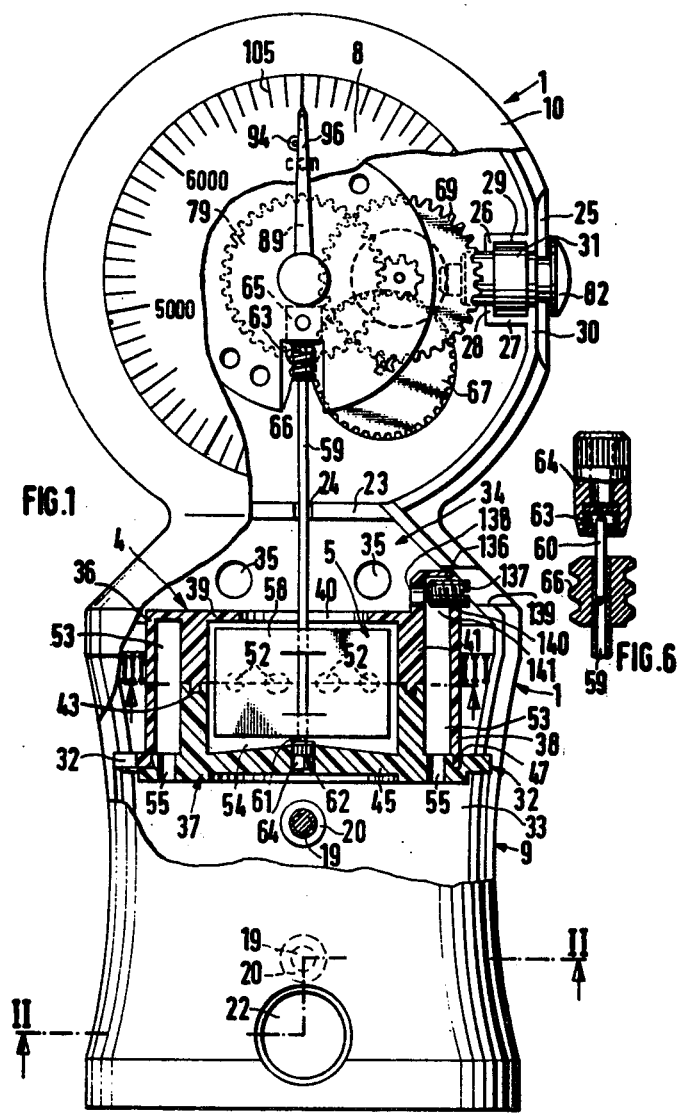

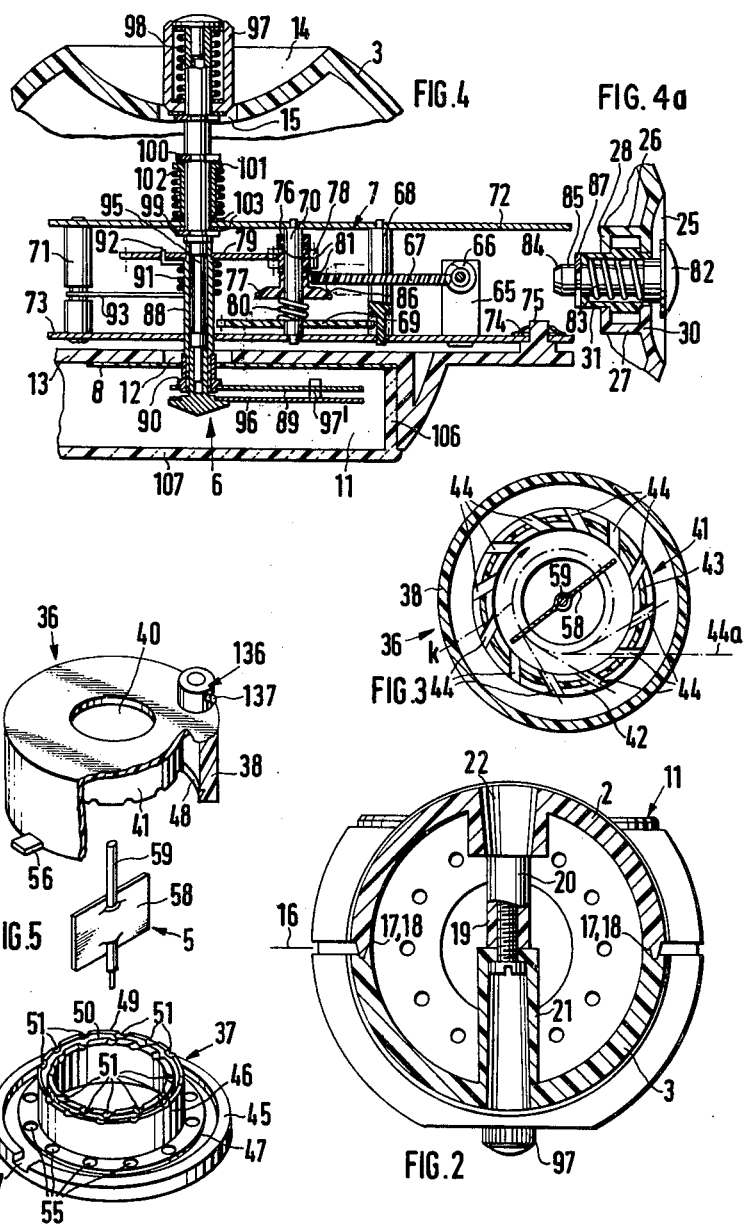

SPIROMETER

FIELD AND BACKGROUND OF THE INVENTION

This invention relates in general to the construction of spirometers and, in particular, to a new and useful spirometer which includes a double-ring rotor blade which is rotated by blowing air directed radially thereagainst to advance both a pointer and a drag pointer, which includes means for driving the pointer through a reduction gearing which permits disconnection of the pointer and, wherein, the pointer is returnable to zero by a return spring, and the drag pointer may be separately returned to zero by a manual manipulation.

DESCRIPTION OF THE PRIOR ART

The present invention relates to a spirometer comprising a housing which encloses an antechamber having a blow-in opening, and a cylindrical turbine chamber which has at least one outlet opening and communicates with the antechamber through a plurality of bores provided in an intermediate wall and in which an air wing rotor is mounted on a shaft by which a pointer rotatable over a circular scale is driven through a reduction gearing, the shaft being supported, by one end in a bearing of the intermediate wall and, by its other end, in a plate of the reduction gearing.

In a known spirometer of this kind, a single pointer is provided with the axis disposed coaxially of the axis of the air wing rotor, and it is rigidly coupled to the air wing rotor through a reduction gearing comprising two spur gears and two pinions, and has a total reduction ratio of 289 : 1. The air wing rotor itself comprises a fan wheel formed by a disc having a plurality of obliquely radially extending blades formed on its periphery and it is secured to the rotor shaft in a plane normal thereto by means of a box screw and a nut. An intermediate wall is provided between the fan wheel and the antechamber of the housing, having a plurality of bores which are arranged around the bearing axis of the rotor shaft at a small radial distance therefrom and extend in parallel to the rotor axis. The intermediate wall is provided with a cylindrical wall which extends up to the plane of the fan wheel and surrounds all of the bores, and the fan wheel is supported in the operation position of the apparatus on the cylindrical wall. The shaft of the fan wheel is mounted for axial displacement so that with the blown-in air flowing from the antechamber into the turbine chamber, the fan wheel is lifted from the cylindrical wall to be rotated by the air flowing radially through the blades.

Aside from the fact that this prior art spirometer is operative only in a definite position, namely, with the rotor axis in a vertical position, a minimum flow pressure is necessary to overcome the weight of the entire air wing rotor and to lift the fan wheel from the cylindrical wall in the turbine chamber, and such pressure frequently cannot be produced by the person to be tested, particularly not at the end of the blowing period. This means that certain air volumes cannot be registered by the apparatus and the measuring accuracy in such cases does not meet requirements therefor. A further disadvantage is that the pointers of this apparatus cannot be returned into their zero positions after the measuring operation unless an attempt is made to zero the pointer by a new, correspondingly metered, blowing operation. In view of the above mentioned basic function, this is not only complicated and time-consuming, but also dependent to a large extent on whether the respective person would succeed in an accurate metering of the air blow necessary for zeroing the pointer. In addition, this known spirometer does not offer the possibility of providing comparative measurements between two consecutive tests without losing the former indication by the new movement of the pointer, if it is not otherwise recorded.

SUMMARY OF THE INVENTION

The present invention is directed to a spirometer which provides a higher accuracy of measurement, is usable in any position, and makes it possible to start each measuring operation with the pointer in its zero position and to perform direct comparative measurements.

To this end, in accordance with the invention, the reduction gearing is equipped with a disengaging coupling actuable by means of a manually operated member, and the pointer is provided with a zero return spring as well as with a drag pointer which can be returned to zero separately, and the air wing rotor comprises a double-wing rotor blade which extends in parallel to the axis of the rotor and against which the air flow is directed radially obliquely. In this design, the positional independence of the appratus results from the possibility of mounting the air wing rotor fixed in its axial direction. The higher accuracy of measurement as compared to the spirometer of the prior art follows firstly, from a substantially improved coupling of forces between the air flowing through the turbine chamber and the air wing rotor and, secondly, from the fact that except for the pure frictional forces which can be minimized by an appropriate mounting of the rotor shaft and the other component parts of the reduction gearing, the air flowing through the turbine chamber encounters no resistance to be overcome. Also particularly advantageous is the simple manner of zeroing the pointer which, because of the provision of a drag pointer, must always take place in reverse motion and, for this purpose, a zero return spring is used. Further, the fact that the drag pointer which stops at the end of each measuring operation and must be zeroed manually, indicates the measured value until it is displaced either by the measuring pointer during a new measuring operation or by hand. Consequently, the inventive spirometer offers considerable advantages both in comparison with the prior art as to its handling and use in practice, and as to its accuracy in measurement, which makes it a valuable measuring instrument even if rigorous scientific standards are applied.

The preferred embodiment of the disengaging coupling, according to the invention, not only has the advantage of being very simple in manufacture, but also the advantage which favorable influences the accuracy of measurement, that the masses to be moved by the return spring during the zeroing of the pointer and the bearing frictions to be overcome are very small, since only the parts directly connected to the pointer shaft are to be moved during this operation. None of the other component parts of the transmission participate therein. This also makes it possible to provide a very compliant return spring, so that, during the measuring operation, a very small torque is opposed to the pointer drive.

The pushbutton provided for actuating the disengaging coupling, in accordance with the invention, is a very simple and reliable mechanism for ensuring the zero setting of the pointer and very inexpensive in manufacture.

In order to obtain a minimum friction in the movement of the drag pointer during the measuring operation and also to fix the drag pointer in a satisfactory manner at the end of such an operation, it is advisable to provide a design in which the pointer shaft is a hollow shaft and is mounted for rotation on a drag pointer shaft having a friction brake and a zero return knob. A friction coupling is provided between the zero return knob and the drag pointer shaft and it serves as an overload protection preventing damages.

The design and arrangement of the return spring, which is helical, offers the advantage of a simple manufacture even with very small tolerances in the spring characteristics, in which connection, it is particularly important to provide a spring with a load-deflection curve as flat as possible, in order to obtain an as constant as possible small torque acting on the pointer shaft over the entire range of rotation of the pointer.

A very important embodiment is that concerning the measuring accuracy wherein there is a kinematic connection between the air wing rotor and the reduction gearing which includes self-locking angle gearing. This design ensures that due to the self-locking property of the angle gear, the kinetic mass forces of the reduction gearing cannot positively effect the results of measurement. Another advantage of this design is that due to the provision of an angle gear between the reduction gearing and the rotor shaft, the plane of rotation of the pointer and, thereby, the plane of the dial can be provided parallel to the axis of the air wing rotor, which is also advantageous in the use of the apparatus.

Further features having a favorable effect on the accuracy of measurement and also on the manufacturing possibilities are also present.

Accordingly, it is an object of the invention to provide a spirometer in which an air wing rotor having double wings is positioned in a separate turbine chamber of a housing which has an antechamber provided with a blowing inlet and an annular portion which communicates with the antechamber or is a part thereof and which surrounds the turbine chamber and is connected thereto by passages which direct the air obliquely against the rotor, and wherein, the rotor is connected through a differential gearing to a pointer which is disengageable from the drive connection and returnable to zero by a return spring, and which further includes a drag pointer which may be separately returned to zero manually.

A further object of the invention is to provide a spirometer which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there is illustrated a preferred embodiment of the invention.

BRIEF DESCRIPTION OF THE DRAWINGS

In the Drawings:

FIG. 1 is a front view, partly in section, of a spirometer constructed in accordance with the invention;

FIG. 2 is a sectional view taken along the line II—II of FIG. 1;

FIG. 3 is a sectional view of the body forming the turbine chamber, taken along the line III—III of FIG. 1;

FIG. 4 is a partly developed, sectional view of the reduction gearing and the pointer mechanism;

FIG. 4a is a sectional view of the zero setting knob assembly.

FIG. 5 is an exploded perspective view of the component parts of the body forming the turbine chamber; and FIG. 6 is an enlarged sectional view of a mounting of the rotor shaft.

DESCRIPTION OF THE PREFERRED EMBODIMENT

Referring to the drawings in particular, the invention embodied therein, comprises a spirometer which is of a compact design and which has a pointer and a drag pointer for indicating a person's expiration rate which is of a size which may be grasped easily in the user's hand and positioned to facilitate blowing therein for obtaining accurate expiration information.

As shown in the drawings, the inventive spirometer comprises a housing 1 assembled of two half-shells 2 and 3, which includes a turbine chamber 4. An air wing rotor 5 is positioned in the housing along with a pointer mechanism 6 with a reduction gearing 7, and a dial 8 which is defined on the housing front face.

The outer shape of housing 1 is that of a body of revolution having a lower part 9 which is slightly necked in the manner of a handle, and a spherical head part 10 of which the respective portions are formed integrally with half-shells 2 and 3. Head part 10 is formed with a cylindrical recess 11 on its front side (see FIG. 4), having a mounting bottom 13 which is provided with a central bore 12 and, on its back side, head part 10 is formed with a spherical cavity 14 provided with a bore 15 which is coaxial of central bore 12. The parting plane 16 of half-shells 2 and 3 extends centrally through housing 1 in parallel to mounting bottom 13 of frontal recess 11 and, in this plane, the two half-shells engage each other in a peripherally extending slot-and-feather joint 17/18. The two half-shells 2 and 3 are connected to each other by screws 19, of which only two are shown in the drawing. For receiving screws 19, half-shell 3 is provided with cylindrical, inwardly directed, hollow pins 21 in the lower part 9 of the housing, and half-shell 2 is provided with hollow pins 20 which are coaxial thereof. Half-shell 2 is provided, in addition, in its lower portion, with a conical blow-in opening 22 into which a mouth fitting piece (not shown) of a flexible blow tube can be inserted. An intermediate wall 23 is provided between the interior of lower part 9 of the housing and the interior of head part 10, having a central bore 24. At the level of the horizontal central plane of head part 10, a concavity 25 is worked into both half-shells 2, 3, at the inside of which a cavity 29 is formed by wall portions 26, 27, 28, and coaxial, semicircular recesses are provided in the opposite front surfaces of wall portion 28 and housing wall 30, for receiving a bearing bush 31.

Housing 1 is provided with an inner circular groove 32 in a plane extending slightly above the half height of lower part 9 of the housing, in which the turbine casing 4, described in more detail in the following, is fixed in a manner such that an airtight separation of an antechamber 33 located below and into which blow-in opening 22 opens, and a cavity 34 located above and provided with a plurality of outlet openings 35, is ensured.

As best seen in FIGS. 1, 3 and 5, turbine casing 4 is assembled of two parts 36 and 37, which are form-locked with each other. Upper part 36 comprises a cylindrical hollow body with a cylindrical outer wall 38 extending over the whole axial length, a front wall 39 which is provided with a central bore 40, and a cylindrical inner wall 41 which is thicker than outer wall 38 and extends approximately up to half the axial length of outer wall 38 and terminates in a plane which is parallel to the upper front wall. The lower front face 42 of inner wall 41 is provided with a central circular rib 43 which has a rectangular cross-section and is interrupted by a plurality of semicylindrical grooves 44 which are uniformly spaced from each other and extend obliquely radially through the entire thickness of inner wall 41. The axes 44a of the semicylindrical grooves, indicated in FIG. 3 in dash-dotted lines, are tangent to a circle k, also indicated in FIG. 3 in dash-dotted lines, having a diameter which is approximately two thirds of the inside diameter of inner wall 41.

Part 37 comprises a circular bottom 45, a wall 46 in the form of a hollow cylinder having a diameter and thickness corresponding to that of inner wall 41, and a circular groove 47. The inner face of this groove is conically backed-off to lockingly receive the lower end of the cylindrical outer wall of the part 36 which is provided, on its inside, with a conical circular indentation 48. The upper front face 49 is provided with a circular groove 50, the cross-section of which corresponds to that of the circular rib 43 of inner wall 41 and it is provided with the same number of obliquely radially extending semicircular grooves 51 as the front face 42 of inner wall 41. After the parts 36 and 37 are assembled with each other, the grooves form obliquely radially extending cylindrical bores 52, which establish communication between turbine chamber 54 and an annular chamber 53 (see FIG. 1) which is formed between the inner walls 41 and 46 and the cylindrical outer wall 38.

Axial bores 55 are provided in the intermediate space between circular groove 47 and wall 46, and they are uniformly distributed around wall 46 and establish communication between antechamber 33 and the annular chamber 53 of turbine casing 4. In order to ensure that upon assembly, the semicylindrical grooves 44 and 51 of parts 36 and 37 register with each other, outer wall 38 is provided with a radially projecting tongue 56, and bottom 45 is provided with a radial slot 57 receiving the tongue. The design of turbine casing 4 in two parts makes it possible, first, to manufacture the casing in an injection-molding process and, second, to insert the air wing rotor 5 into the turbine chamber 54, which has a radial extension which is larger than the diameter of bore 40 provided in front wall 39 of turbine casing 4 (FIG. 1). Turbine casing 4 is form-locked in housing 1, because the rim of bottom 45 is engaged in inner circular groove 32 of the lower part 9 of housing 1.

Air wing rotor 5 comprises a thin, rectangular plate 58, the length and width of which are by about 0.5 to 2.00 mm smaller than the clear dimensions of turbine chamber 54, and a hollow shaft 59 to which plate 58 is non-rotatably secured in a manner indicated in FIGS. 1, 3 and 5.

As may be learned from FIG. 6, both ends of hollow shaft 59 are provided with bearing pins 60 and 61 which are press-fitted therein and by means of which the shaft is supported, on its one end, in a jewel bearing 62 of bottom 45 of turbine casing 4 and, on its other end, in a jewel bearing 63 for easy rotation. The two jewel bearings 62 and 63 are received in mounts 64. The upper one is seated in a bearing block 65 and the lower one in bottom 45. The upper end of hollow shaft 59 carries a worm 66 non-rotatably fixed thereto which meshes with a worm wheel 67. Worm wheel 67 is secured to a pinion shaft 68, the pinion of which meshes with a gear 69, which is non-rotatably carried on a shaft 70. Pinion shaft 68 and shaft 70 are mounted for rotation on two bearing plates 72 and 73 which are connected to each other by a plurality of columns 71 and are secured, by means of retaining spring washers 74, to cylindrical studs 75 of mounting bottom 13 (FIG. 4).

A thrust ring 76 is press-fitted to the end of shaft 70 opposite to gear 69. Between thrust ring 76 and a flanged bushing 77 which is mounted for rotation and axial displacement on shaft 70, a pinion 78 meshing with a gear 79 is loosely carried on shaft 70. A compression spring 80 is received on shaft 70 between flanged bushing 77 and gear 69, by which flanged bushing 77 is biased in the axial direction against pinion 78 and thrust ring 76. Friction washers 81 are inserted on both sides of pinion 78, by which a nonslip frictional connection is ensured between thrust ring 76 and pinion 78. The parts 76 through 81 form a disengaging coupling which is actuable by means of a pushbutton 82 (see FIG. 4a) movable in the radial direction toward shaft 70. Pushbuttom 82 is mounted for axial displacement in bearing bush 31 against the action of a compression spring 83 and in a manner such that the conical end portion 84 of its shank 85 cooperates with a conical annular surface 86 of flanged bushing 77, thereby, effecting an axial displacement of flanged bushing 77 and, consequently, an interruption of the force transmission between shaft 70 and pinion 78. Pushbutton 82 is held in bearing bush 31 by means of a retaining ring 87.

Gear 79 meshing with pinion 78 is secured firmly to a hollow shaft 88 which is mounted for rotation in plate 73 and extends through bore 12 of mounting bottom 13 of the frontal half-shell 2. The shaft 88 carries a pointer 89. Pointer 89 is secured to hollow shaft 88 by means of a bushing 90. Hollow shaft 88 also carries a helical spring 91 having a larger diameter. One end 92 of helical spring 91 is suspended from a bore of gear 79, while the other end 93 of helical spring 91 is secured to column 71. Helical spring 91 serves as a return spring for pointer 89 which, in its zero position, rests against a stop pin 94.

A drag pointer shaft 95 is mounted for rotation relative to shaft 88 within hollow shaft 88. On its one end, drag pointer shaft 95 is equipped with a drag pointer 96, which is provided with a driving lug 97' projecting into the plane of motion of pointer 89. On the other end of the shaft 95 which extends through bore 15 of half-shell 3, there is a rotary knob 97 which serves the purpose of zero-setting drag pointer 96. Rotary knob 97 is connected to drag pointer shaft 95 by the frictional pressure exerted by a compression spring 98, so that the knob relative to the drag pointer shaft when drag pointer 89 is in its zero position and applies against the stop pin 94. Drag pointer shaft 95 is mounted for rotation in plate 72 and is secured against axial displacement by two locking washers 99 and 100. Locking washer 99 is located at the inside of plate 72, while locking washer 100 is provided at a location spaced from the outside of plate 72, and an axially displaceable flanged bushing 101, mounted for rotation on drag pointer shaft 95 is provided, which is surrounded by a compression spring 102. Friction washers 103 are provided on both sides of plate 72, which cooperate with compression spring 102, flanged bushing 101, and the two locking washers 99 and 100 to form a friction brake for drag pointer shaft 95 and, thereby, for drag pointer 96. Both compression spring 91 and compression spring 102 are compliant to an extent such that they oppose a minimum resistance to the pointer drive mechanism but, on the other hand, are capable, with the coupling disengaged, of returning pointer 89 into its zero position, as well as of preventing drag pointer 96 from being automaticaly displaced, for example, by shocks.

The circular dial 8 is provided at the outside of mounting bottom 13, bearing a circular graduation 105 and is held in place by the cylindrical wall 106 of a transparent cover 107 which closes the opening of recess 11. Wall 106 is slightly force-fitted in the cylindrical recess 11.

The operation of the inventive spirometer is as follows: First, with pointers 89 and 96 in their zero positions, breathing air is blown by the person to be tested through a flexible tube and through bore 22 into antechamber 33. The breathing air blown passes through bores 55 into annular chamber 53 and, therefrom, through the obliquely radial bores 52, into turbine chamber 54, where it puts air wing rotor 5 and shaft 59 into rotary motion. Through the described reduction gearing 7, this rotary motion is transmitted to pointer 89 and, therefrom, to drag pointer 96, so that the latter moves clockwise (as viewed in FIG. 1) over scale 105. The air flowing into turbine chamber 54 leaves through bore 40 and flows into cavity 34, wherefrom, it escapes through bores 35 to the outside. To prevent moisture contained in the breathing air from passing into the cavity of head part 10 and condensing on the metal parts of reduction gearing 7, it is important to provide a minimum possible diameter of bore 24 in intermediate wall 23.

Since, according to experience, the blow pressure decreases continuously with the blowing time, the speed of the air wing rotor drops correspondingly, until the air wing eventually stops if the lungs volume of the expiring person is exhausted. Taking this fact into account, the inventive design ensures that the result of measurement is not invalidated by errors caused by centrifugal forces due to the provided small weight and, consequently, small kinetic mass forces of the air wing rotor 5 and hollow shaft 59, and due to the fact that a gear reduction embodied by worm 66 and worm wheel 67, self-locking in the direction of the force transmission is provided between hollow shaft 59 and the reduction gearing 67 through 79. With the air in turbine chamber 54 stagnant, a satisfactory braking force is also exerted by the stagnation air on the air wing rotor. On the other hand, due to the numberous obliquely radial bores 52 and to the cross-sectional shape of thin plate 58 adjusted to the turbine chamber 54 as described, an optimum non-positive force transmission is obtained between the air stream flowing in and the air wing rotor.

Upon terminating the measuring operation by actuating pushbutton 82, pointer 89 can be returned into its zero position, while drag pointer 96 due to the action of friction brake 99 through 103 remains in place, and continues to indicate the result of measurement. The operator is now free to choose whether to keep drag pointer 96 in its present position up to the next measuring operation in order to have the possibility of a direct comparison with the previous measurement, or to return drag pointer 96 into its zero position also, by correspondingly turning rotary knob 97. It may be returned to zero, for example, if the operator is going to test another person.

The total reduction rate of the reduction gearing is 3600:1, i.e., 3600 revolutions of air wing rotor 5 are necessary for a single revolution of pointer 89. This high reduction ratio ensures a very high resolution, thus measuring accuracy and, also, prevents the resistance forces of the zero return spring 91 and the drag pointer friction brake washers 99 through 103 from producing a negative effect on the measuring accuracy.

To make the spirometer capable of calibration, i.e., for example, to be able to compensate or eliminate the deviations from proportionality, due to manufacture, of the speed of the air wing rotor depending on the rate of flow, the annular chamber 53 surrounding turbine chamber 54 is provided with a bypass air outlet 138 which opens into cavity 34 and which can be closed to a selected degree by means of a screw 137. This bypass air outlet 138 is designed as a radial bore provided in the wall of a cylindrical extension 136 of upper part 36 of turbine casing 4. The cavity 141 of cylindrical extension 136 has a diameter corresponding to the cross-sectional width of annular chamber 53 and communicates directly with chamber 53. Screw 137, which has a slightly larger nominal diameter than bypass air outlet 138, is screwed into a threaded hole 140 which is located diametrically opposite to outlet 138 and its coaxial therewith. By turning screw 137 in one or the other direction, the end facing outlet 138 of screw 137 can be moved closer to or farther away from the bore rim thereof so that the passageway between the screw and the outlet can be enlarged or reduced, thereby, increasing or reducing the bypass effect. In order to make screw 137 accessible for adjusting or calibrating the apparatus, an opening 139 is provided at the respective location in housing 1.

There is a condition, however, for applying this method of calibration, namely, that rotor 5 and turbine casing 4, as well as reduction gearing 7, must be dimensioned so that with bypass air outlet 138 closed, a small proportionality in excess exists between the speed and the volumetric flow rate, i.e., that with outlet 138 closed, pointers 89 or 96 indicate on dial 104 slightly more, for example 3% to 5% more, than would correspond to the actually measured air volume, and that by opening the bypass air outlet 138 to an extent such that the portion of the air volume to be measured corresponding to the indication in excess or error cannot pass through turbine chamber 54 but passes through outlet 138 into cavity 34 and therefrom through openings 35 to the outside, the measuring error can be compensated.

In the embodiment shown in FIG. 1, for reasons of simple illustration, the cylindrical extension 136 with the bypass air outlet and adjusting screw 137 are arranged so that an additional opening 139 is needed in the housing wall. In practice, however, the cylindrical extension may be located so that set screw 137 is accessible through one of the already provided air outlet openings 35. In this case, opening 139 can be omitted.

The calibration itself is done so that, with the aid of another volume measuring device, definite air volumes are blow through the spirometer and the respective indication as compared with the desired indication. Then, by correspondingly adjusting screw 137 relative to bore 138, the determined measuring error is eliminated. Only with the possibility of calibrating the device and thereby ensuring a higher accuracy of measurement and indication is the applicability of the spirometer substantially increased and rendered more important, so that it can be used also as a medical measuring instrument, for example, and also as an auxiliary diagnostic apparatus.

In a modification of the arrangement of the just-described bypass air outlet 138 in connection with the annular chamber surrounding the turbine chamber, it is also possible, in principle, to provide the bypass air outlet in connection with antechamber 33. In addition, it is possible to design the bypass air outlet as an axial bore of a set screw which, for example, is radially screwed into outer wall 38 of annular chamber 53 and the inner, circular, front face of which is adjustable relative to the cylindrical outside surface of wall 41 of turbine chamber 54. In this case, to close the bypass air outlet, the hollow screw has to be screwed radially inwardly until its inner front face applies against the outside surface of wall 41 of turbine chamber 54.

While a specific embodiment of the invention has been shown and described in detail to illustrate the application of the principles of the invention, it will be understood that the invention may be embodied otherwise without departing from such principles.

What is claimed is:

1. A spirometer, comprising a housing having walls defining a cylindrical turbine chamber, an antechamber having a blow-in opening and having an annular portion around said cylindrical turbine chamber and a plurality of passages extending from the annular portion tangentially into the turbine chamber, a small-diameter shaft extending into said turbine chamber and centrally mounted for free rotation therein, an air wing rotor secured to said small-diameter shaft and located in said turbine chamber for rotation by the blowing air directed in through the blowing opening and said antechamber and through the passages into the turbine chamber, said air wing rotor comprising a thin flat plate which is at least approximately conformable to the inner contour of said cylndrical turbine chamber, said plate being centrally secured to said small-diameter shaft, said cylindrical turbine chamber including a cylindrical wall of said housing having a space therearound and provided with said passages which comprise obliquely radially extending air inlet openings distributed around the circumference thereof, said space around said cylindrical wall defining said annular chamber portion, said housing having at least one outlet opening from said cylindrical turbine chamber to the outside, said housing having a portion with a dial having indications thereon, a pointer shaft with a pointer and a drag shaft with a drag pointer rotatably mounted in said housing over said dial, said pointer and said drag pointer being movable over the dial to indicate the blowing rate, a high-ratio reduction gearing connected between said small-diameter shaft and said pointer shaft and said drag shaft to rotate said pointer and said drag pointer upon rotation of said shaft, a manually operable, disconnectable coupling means connected between said shaft and said pointer shaft for disengaging said pointer shaft, a zero return spring means acting on said pointer shaft to bias it towards a zero position, a return knob connected to said drag shaft for moving said drag pointer manually back to zero separately from said pointer, and frictional brake means connected between said drag shaft and said housing for resisting the movement of said drag shaft, said thin flat plate forming a double-wing rotor blade positioned in said cylindrical turbine chamber at a location such that air from said obliquely radially extending air inlet openings is directed radially obliquely against said rotor blade to rotate said small-diameter shaft, wherein said housing includes a hollow cylindrical two-part body, said parts being formed lockably engageable and having a lower handle portion defining said turbine chamber and and said antechamber and an upper dial-forming portion joined to said handle portion, said annular chamber portion having a closed bottom wall and a top wall with a central opening therein defining the turbine chamber, said annular chamber portion around said turbine chamber being separable along a median plane into upper and lower portions, said bottom having bores therethrough communicating said antechamber to said annular chamber portion, said passages being defined at the separating plane of the wall portion defining the boundaries of said turbine chamber.

2. A spirometer, according to claim 1, wherein said reduction gearing includes a pinion, a transmission shaft loosely carrying said pinion, said means rotatably supporting said pointer including a pointer shaft having a fixed gear thereon engageable with said pinion, a flange bushing rotatable on said transmission shaft, a spring biasing said bushing toward said pinion, a thrust ring secured to said transmission shaft against which said pinion is movable, said flange bushing being axially displaceable on said transmission shaft, said disengageable coupling means including a pushbutton mounted for movement on said housing and being accessible on the exterior of said housing and being engageable against said flange bushing to move it axially along said transmission shaft to disengage said pinion from the gear fixed to said pointer shaft.

3. A spirometer, according to claim 2, including means resiliently mounting said pushbutton in said housing, said pushbutton having a shank end engageable with the flange of said flange bushing.

4. A spirometer, according to claim 1, wherein said pointer shaft comprises a hollow shaft, said hollow shaft being mounted for rotation on said drag shaft, a friction brake associated with said drag shaft for holding said drag shaft at a rotated position, said return knob means comprising a return knob connected to said drag shaft and located outside of said housing to permit its manual turning to return said drag shaft with said drag pointer to a zero position.

5. A spirometer, according to claim 4, wherein said return knob is rotatably mounted on said drag shaft, and a friction coupling frictionally connected between said draft shaft and said return knob.

6. A spirometer, according to claim 5, wherein said zero return spring means comprises a helical spring disposed concentrically with radial play around said pointer shaft, said spring helical having one end secured to said reduction gearing and another end fastened to said housing.

7. A spirometer, according to claim 1, wherein said reduction gearing comprises an angle gearing which is self-locking in a direction opposite to the force transmission and comprises a worm carried on said shaft and a worm wheel meshing therewith.

8. A spirometer, according to claim 1, wherein said shaft carrying said air wing rotor comprises a thin-walled, small diameter tube, a roller-burnished bearing pin in each of said tube, a jewel bearing at each end of said shaft rotatably supporting said bearing pins.

9. A spirometer, according to claim 1, wherein said bottom wall defining the turbine chamber includes an annular extension portion having a circular groove therein, said exterior jacket wall being mounted in said groove.

10. A spirometer, according to claim 1, including a turbine casing in said housing forming said turbine chamber and said annular portion including an inner wall portion surrounding said turbine chamber and an outer wall portion surrounding said annular portion spaced outwardly from said inner wall portion, said casing being divided along a separating plane and comprising two interlocking parts.

11. A spirometer, according to claim 10, wherein said interlocking parts are engaged with each other by means of peripherally extending a slot and feather joint edges, said parts being securable together by screws, said housing comprising two half portions which are interengageable and including a handle-forming portion and a dial-forming portion, said dial-forming portion including an exterior face with a dial disposed in a plane extending parallel to the parting plane of said housing parts and parallel to the axis of said turbine chamber and being further provided with stud portions which extend inwardly into said housing and provide bores for the securing of said parts together.

12. A spirometer, according to claim 1, wherein said reduction gearing has a reduction transmission ratio of 3000:1.

13. A spirometer, according to claim 1, including means defining a bypass air outlet from said antechamber to the outside and means for adjusting the area of said bypass outlet.

14. A spirometer, according to claim 1, including means defining a bypass outlet connected to said annular portion, an adjustable screw extending into said bypass outlet for varying the opening of said outlet.

* * * * *